US012593976B2

(12) United States Patent
Nie

(10) Patent No.: US 12,593,976 B2
(45) Date of Patent: Apr. 7, 2026

(54) SYSTEMS AND METHODS FOR MEASURING VISUAL AXIS OF THE EYE

(71) Applicant: Xiaochun Nie, Mountain View, CA (US)

(72) Inventor: Xiaochun Nie, Mountain View, CA (US)

( * ) Notice: Subject to any disclaimer, the term of this patent is extended or adjusted under 35 U.S.C. 154(b) by 421 days.

(21) Appl. No.: 18/194,532

(22) Filed: Mar. 31, 2023

(65) Prior Publication Data

US 2023/0240528 A1 Aug. 3, 2023

Related U.S. Application Data

(63) Continuation of application No. PCT/US2021/043875, filed on Jul. 30, 2021.

(60) Provisional application No. 63/090,543, filed on Oct. 12, 2020.

(51) Int. Cl.
| | |
|---|---|
| *A61B 3/10* | (2006.01) |
| *A61B 3/02* | (2006.01) |
| *A61B 3/113* | (2006.01) |
| *A61B 3/12* | (2006.01) |
| *A61B 3/14* | (2006.01) |

(52) U.S. Cl.
CPC ................ *A61B 3/113* (2013.01); *A61B 3/14* (2013.01)

(58) Field of Classification Search
CPC ......... A61B 3/02; A61B 3/102; A61B 3/1025; A61B 3/113; A61B 3/1015; A61B 3/1225; A61B 3/024; G06F 3/017; G06F 3/012; G06F 3/013; G06K 9/00; G02B 2027/0138; G02B 2027/0187; G02B 7/0093; G06T 7/73; G06T 2207/30201
USPC ....... 351/205, 200, 206, 209, 210, 221–223, 351/245–246
See application file for complete search history.

(56) References Cited

U.S. PATENT DOCUMENTS

| | | | |
|---|---|---|---|
| 2007/0015611 A1* | 1/2007 | Noble ................... | A61B 5/1126 |
| | | | 473/450 |
| 2013/0178287 A1 | 7/2013 | Yahav | |
| 2016/0063303 A1 | 3/2016 | Cheung et al. | |
| 2018/0157332 A1 | 6/2018 | Nie | |
| 2019/0005679 A1* | 1/2019 | Nie ........................... | G06T 7/73 |
| 2020/0225745 A1 | 7/2020 | Molin et al. | |
| 2020/0319708 A1 | 10/2020 | Nie | |
| 2021/0255625 A1* | 8/2021 | Baladhandapani ..... | G10L 15/22 |

* cited by examiner

*Primary Examiner* — Dawayne Pinkney
(74) *Attorney, Agent, or Firm* — IPro, PLLC

(57) ABSTRACT

Disclosed herein are methods for determining an angular offset between a visual axis of a person's eye and an optical axis of the eye, or an angular offset between a line of sight of the eye and the optical axis of the eye.

13 Claims, 3 Drawing Sheets

Image Sensor and Spatial Orientation Sensor

Image Sensor        Spatial Orientation Sensor

Image Sensor and
Spatial Orientation Sensor

Image Sensor

SYSTEMS AND METHODS FOR MEASURING VISUAL AXIS OF THE EYE

BACKGROUND

Eye tracking can be used in a wide range of applications such as human machine interface, gaming, virtual reality, human behavior study and medicine etc.

SUMMARY

Disclosed herein is Method One comprising: letting user look at a gaze point in a distance, obtaining a first orientation of an eye in the image sensor coordinate system CS-C and obtaining a first orientation of a spatial orientation sensor in the world coordinate system CS-W.

After the user moves the head to a different pose but still looks at the same gaze point, obtaining a second orientation of the eye in the image sensor coordinate system CS-C and obtaining a second orientation of the spatial orientation sensor in the world coordinate system CS-W.

Using the first orientation of the eye in the image sensor coordinate system CS-C, the first orientation of the spatial orientation sensor in the world coordinate system CS-W, the second orientation of the eye in the image sensor coordinate system CS-C, the second orientation of the spatial orientation sensor in the world coordinate system CS-W, and the orientation of the image sensor relative to the spatial orientation sensor or the orientation of the spatial orientation sensor relative to the image sensor, the angular offset between the visual axis and the optical axis of the eye in eye coordinate system CS-E is obtained.

For Method One, the image sensor and the spatial orientation sensor may move relative to the user's head and the image sensor and the spatial orientation sensor do not move relative to each other.

The orientation of the image sensor in the spatial orientation sensor coordinate system CS-G is known and does not change.

By looking at the same gaze point with more head poses, more pairs of the orientation of the eye in the image sensor coordinate system CS-C, and the orientation of the spatial orientation sensor in the world coordinate system CS-W can be obtained. These data can be used to further increase the accuracy of the result of the angular offset of the visual axis relative to the optical axis of the eye in eye coordinate system CS-E.

Disclosed herein Method Two comprising: letting user look at a gaze point in a distance, obtaining a first orientation of an eye in the image sensor coordinate system CS-C.

After the user moves the head to a different pose but still looks at the same gaze point, obtaining a second orientation of the eye in the image sensor coordinate system CS-C.

Using the first orientation of the eye in the image sensor coordinate system CS, the second orientation of the eye in the image sensor coordinate system CS-C, the angular offset of the visual axis relative to the optical axis of the eye in eye coordinate system CS-E is obtained.

For Method Two, the image sensor is mounted near the eye and the position and orientation of the image sensor relative the world coordinate system CS-W do not change.

By looking at the same gaze point with more head poses, the orientation of the eye in the image sensor coordinate system CS-C can be obtained. These data can be used to further increase the accuracy the result the angular offset of the visual axis relative to the optical axis of the eye in eye coordinate system CS-E.

Disclosed herein is a computer program product comprising a non-transitory computer readable medium having instructions recorded thereon, the instructions when executed by a computer implementing any of the above methods.

DETAILED DESCRIPTION

Figure 6:
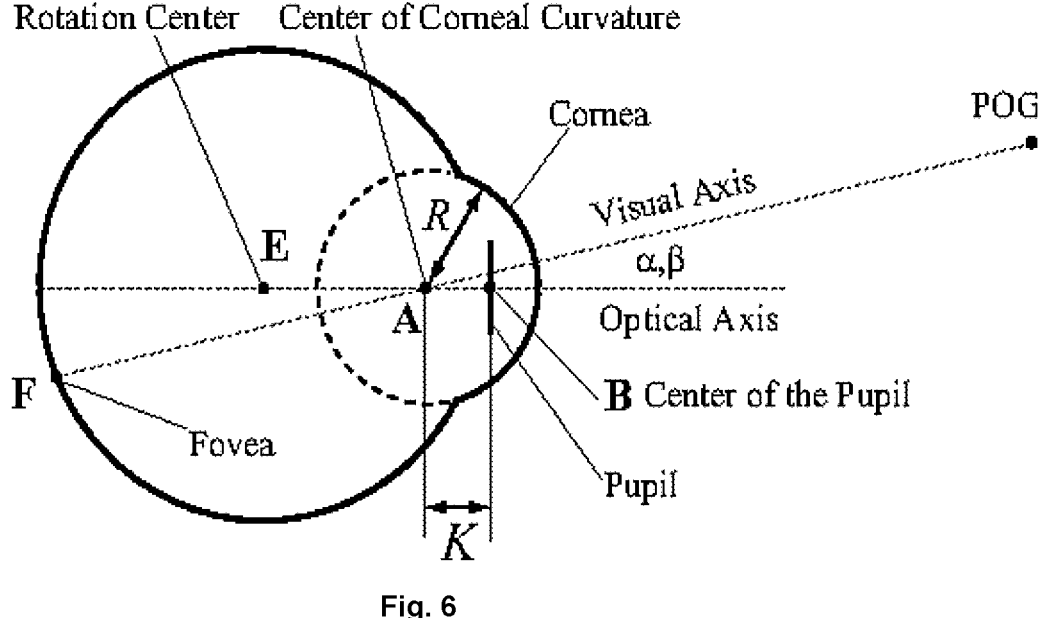
FIG. 6 shows the structure of an eyeball.

An eyeball has an optical axis and a visual axis, as shown in FIG. 6. The optical axis is defined as the line passing the pupil center and the eyeball center. The visual axis is defined as the line passing the center of curvature of the cornea and the fovea. In addition, the line of sight is defined as the line passing the gaze point and the pupil center. The gaze point is the point in the outside world where the eye is looking at.

For a given eye, the visual axis and the optical axis are fixed with respect to that eye. In most eyes, the visual axis and the optical axis are not aligned. And the amount of angular offset between these two axes may vary from eye to eye and from person to person. Therefore, only knowing where the optical axis is pointing to is not sufficient to determine where the user is looking at. The angular offset between these two axes can be represented in a number of ways, such as a pair of Euler angles in an Euler coordinate system, or a 3D vector in a 3D Cartesian coordinate system, or a 3×3 matrix, or a quaternion.

In most eye tracking systems, a manual calibration step is needed to determine the angular offset between the visual axis and the optical axis of the eye directly or indirectly. There can be different approaches to achieve it. Here are some examples. One approach is to require the user to confirm a gaze point by purposely looking at a spot in front of the eye and confirming it afterward in an image recorded from a forward facing camera mounted from the user side. A second approach is to have the eye tracking system to draw a marker on screen and let the user look at it and confirm it. A third approach is to have the eye tracking system to provide a physical marker and let the user look at it and then the eye tracking system records and recognizes it with a forward facing camera mounted from user side. These approaches can be time consuming, error-prone, and they usually require extra hardware and software.

A 3D coordinate system using the right-hand rule is defined in Part A1.1 of the Appendix section. The image sensor coordinate system CS-C using the right-hand rule is defined in Part A1.2 of the Appendix section. The eye coordinate system CS-E using the right-hand rule is defined in Part A1.3 of the Appendix section. The head coordinate system CS-H using the right-hand rule is defined in Part A1.4 of the Appendix section.

The position, orientation and pose of a 3D object in a 3D coordinate system is defined in A1.6. Accordingly, the pose of the user's head includes the position and the orientation of the head.

Mathematical utility functions used in this disclosure are listed in Part A2 of the Appendix section. Quaternion, vector and matrix mathematics is discussed herein. Quaternions are widely used in this disclosure. A function using quaternions can also be expressed using matrices, Euler angles or other suitable mathematic expressions.

In abbreviations in the form of "A_B_C" used in this disclosure: "A" represents the type; "B" represents the specific; "C" represents the context. As an example, an abbreviation "q_e_c" means a quaternion "q" representing the orientation of the eye "e" in the image sensor coordinate system "c". In the abbreviations in the form of "A_B_C": "g" represents the spatial orientation sensor, "w" represents the world and "h" represents the user's head. See Part A2 of the Appendix section. For example, "q_g_w" means a quaternion representing the orientation of the spatial orientation sensor in the world coordinate system; "q_h_w" means a quaternion representing the orientation of the spatial orientation sensor in the head coordinate system. The orientation of an object can be represented by the orientation of a coordinate system fixed to it. For example, the orientation of the eye can be represented by the orientation of the eye coordinate system.

Figure 3:
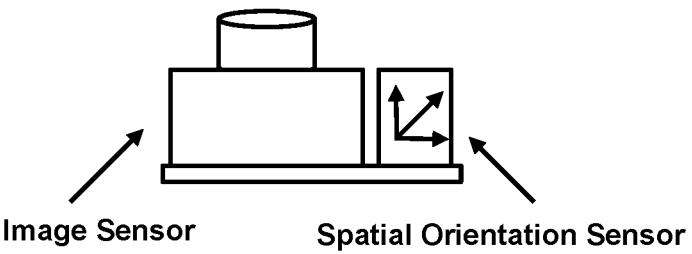
FIG. 3 shows an image sensor and a spatial orientation sensor mounted on a rigid frame.
Figure 4:
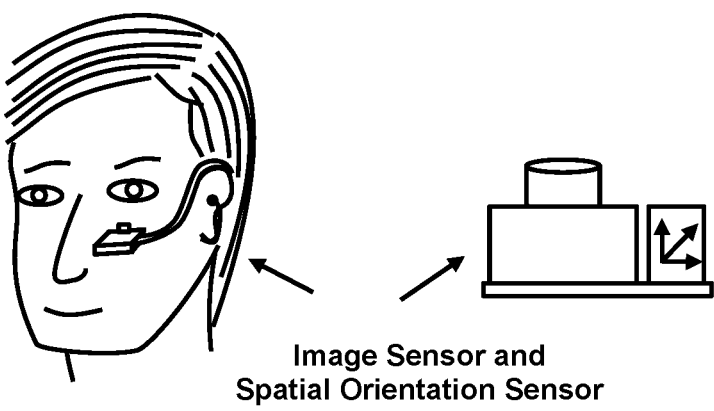
FIG. 4 shows that in one embodiment using Method One, an image sensor and a spatial orientation sensor are attached to a harness frame worn by a user.

In an embodiment using Method One, the user wears an image sensor and a spatial orientation sensor, as shown in FIG. 4. The image sensor can capture images of the user's eye. The image sensor is mounted on a rigid platform with a spatial orientation sensor, as shown in FIG. 3. The orientation q_c_g of the image sensor relative to the spatial orientation sensor coordinate system CS-G is known and does not change. The spatial orientation sensor measures its own orientation (which can be represented by the orientation of the spatial orientation sensor coordinate system CS-G) in the world coordinate system CS-W.

The image sensor and spatial orientation sensor may or may not move with the user's head.

In a measurement, the user looks at a gaze point in a distance, obtaining a first orientation of an eye in the image sensor coordinate system CS-C, and obtaining a first orientation of a spatial orientation sensor in the world coordinate system CS-W.

In another measurement, after the user moves the head to a different pose but still looks at the same gaze point, obtaining a second orientation of the eye in the image sensor coordinate system CS-C, and obtaining a second orientation of a spatial orientation sensor in the world coordinate system CS-W.

The angular offset of the visual axis relative to the optical axis of the eye in eye coordinate system CS-E is obtained, using the first orientation of the eye in the image sensor coordinate system CS, the first orientation of the spatial orientation sensor in the world coordinate system CS-W, the second orientation of the eye in the image sensor coordinate system CS, the second orientation of the spatial orientation sensor in the world coordinate system CS-W, and the orientation of the image sensor in the spatial orientation sensor coordinate system CS-G.

In other words, while the user looks at the same gaze point in a distance at different head poses, the orientations $q\_e\_c\_i$ of the eye relative to the image sensor coordinate system CS-C are obtained and the orientations $q\_g\_w\_i$ of the spatial orientation sensor relative to the world coordinate system CS-W are obtained. Here the suffix "_i" represent the index of the measurement. Therefore pairs of orientation data are obtained as {q_e_c_0, q_g_w_0}, {q_e_c_1, q_g_w_1}, . . . where i=0, 1, . . . . The angular offset of the visual axis relative to the optical axis of the eye in eye coordinate system CS-E is obtained using these pairs of orientation data.

In one embodiment, the visual axis is represented with a unit vector v_a_e in the eye coordinate system CS-E. In each measurement, the visual axis can be represented as a unit vector v_a_w_i in the world coordinate system CS-W, where the suffix "_i" i=0, 1 . . . represent the index of the measurement. Because the user looks at the same gaze point at a distance in each measurement, all the vectors v_a_w_i are the same, where i=0, 1 . . . because the distance between the eye and the gaze point is much bigger than the change of positions of the head between measurements.

Unit vector v_a_e representing the visual axis in the eye coordinate system CS-E can be obtained using 2 or more pairs of measured orientation data {q_e_c_i, q_g_w_i}, i=0, 1 . . . , and the orientation q_c_g of the image sensor relative to the spatial orientation sensor coordinate system CS-G (or the orientation q_g_c of the spatial orientation sensor relative to the image sensor). It is assumed q_c_g is known and stays fixed.

Two pairs of measured orientation data {q_e_c_i, q_g_w_i} where i=0, 1 are sufficient to get a result of the angular offset of visual axis relative to the optical axis. More pairs of measured orientation data will increase the accuracy of the result.

To get better result, when the user changes head poses from one measurement to the next, the head should change its orientation and the head should avoid changing its position. In addition, it is preferable that the change in the orientation is along the Z axis of the head coordinate system CS-H.

The position change of the eye between the different head poses in the image sensor coordinate system CS-C can be also taken into account during each measurement to increase the accuracy of the result, especially when the distance between the eye and the gaze point is not far enough from use.

The position of the image sensor in the world coordinate system CS-W can be also taken into account during each measurement to increase the accuracy of the result, especially when the distance between the eye and the gaze point is not far enough from the user.

Figure 5:
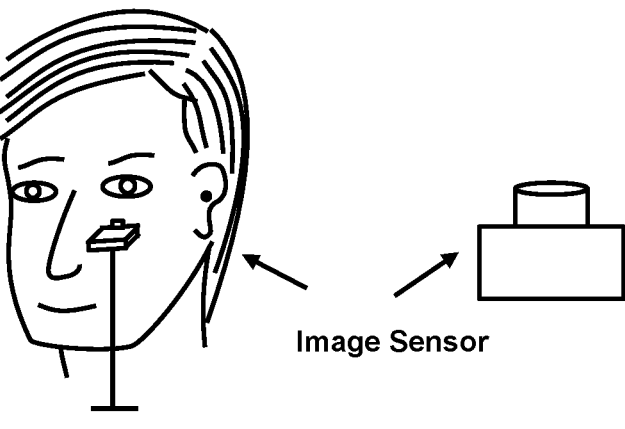
FIG. 5 shows that in one embodiment using Method Two, an image sensor are attached to a rigid platform near the eye of a user. Its position and orientation relative to the world coordinate system is fixed.

In one embodiment using Method Two, the image sensor is mounted (e.g., on a rigid platform) near the user's eye, as shown in FIG. 5. The image sensor relative to the world coordinate system CS-W does not change.

In a measurement, the user looks at a gaze point in a distance, obtaining a first orientation of the eye in the image sensor coordinate system CS-C.

In another measurement, after the user moves the head to a different pose but still looks at the same gaze point, obtaining a second orientation of the eye in the image sensor coordinate system CS-C.

Using the first orientation of the eye in the image sensor coordinate system CS, and the second orientation of the eye in the image sensor coordinate system CS, the angular offset of the visual axis relative to the optical axis of the eye in eye coordinate system CS-E is obtained.

In each measurement, the user looks at the same gaze point in a distance, but at a different head pose, the orientation q_e_c_i of the eye relative to the image sensor coordinate system CS-C is obtained. Here the suffix "_i" represent the index of the measurement. Therefore orientation data are obtained as $q\_e\_c\_0$, $q\_e\_c\_1$, . . . where $i=0$, 1, . . . . The angular offset of the visual axis relative to the optical axis of the eye in eye coordinate system CS-E is obtained using the orientation data.

In an embodiment, the visual axis is represented with a fixed unit vector $v\_a\_e$ in the eye coordinate system CS-E. In each measurement, the visual axis can be represented as a unit vector $v\_a\_w\_i$ in the world coordinate system CS-W, where the suffix "$\_i$" $i=0$, 1 . . . represent the index of the measurement. Because the user looks at the same gaze point at a distance in each measurement, all the vectors $v\_a\_w\_i$, where $i=0$, 1 . . . are the same because the distance between the eye and the gaze point is much bigger than the difference of positions of the head between measurements.

Unit vector $v\_a\_e$ representing visual axis in the eye coordinate system CS-E can be obtained using 2 or more measured orientation data $q\_e\_c\_i$, where $i=0$, 1 . . . .

Two measured orientation data $q\_e\_c\_i$ where $i=0$, 1 are sufficient to get a result of the angular offset of visual axis relative to the optical axis. More measured orientation data will increase the accuracy of the result.

To get better result, when the user changes head poses from one measurement to the next, the head should change its orientation and the head should avoid changing its position. In addition, it is preferable that the change in the orientation is along the Z axis of the head coordinate system CS-H.

The position change of eye in image sensor coordinate system CS-C can be also taken into account during each measurement to increase the accuracy of the result, especially when the distance between the eye and the gaze point is not far enough from use.

The position of image sensor in world coordinate system CS-W can be also taken into account during each measurement to increase the accuracy of the result, especially when the distance between the eye and the gaze point is not far enough from the user.

Figure 2:
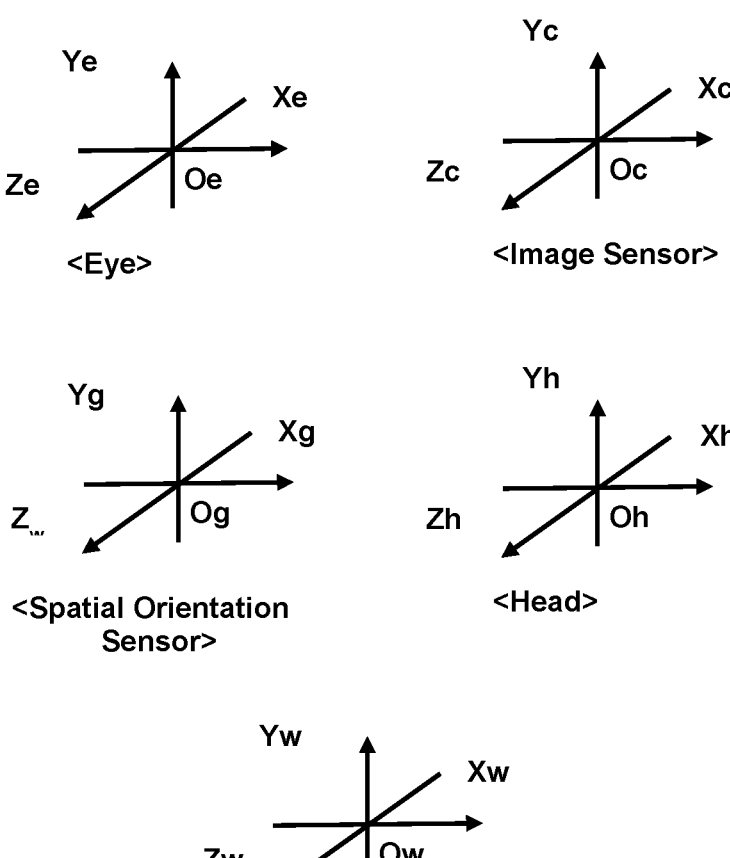
FIG. 2 shows several 3D coordinate systems referred to herein.

This disclosure refers to the following coordinate system as shown in FIG. 2. They are defined as:

The image sensor coordinate system Xc-Yc-Zc-Oc: CS-C is defined in A1.2.

The eye coordinate system Xe-Ye-Ze-Oe: CS-E is defined in A1.3

The head coordinate system Xh-Yh-Zh-Oh: CS-H is defined in A1.4

The spatial orientation Sensor coordinate system Xg-Yg-Zg-Og:CS-G

The world coordinate system Xw-Yw-Zw-Ow:CS-W
System Hardware, Software and Configuration An imaging sensor measures both brightness and color of light. A camera is one kind of imaging sensor. Other kinds of imaging sensors can be used here in similar ways. A camera can be of color, grayscale, infrared or non-infrared, etc. Parameters of a camera include its physical dimensions, resolution and focal length of the lens mounted etc. The imaging sensor referred in this disclosure can be a single camera, an array of cameras, or a combination of different image sensing devices.

A spatial orientation sensor measures the orientation of its coordination system CS-G in the world coordinate system CS-W.

Head Gear. The apparatus to fix the image sensors and other sensors to the user's head. It can be a glasses frame, a head band or a helmet, etc., depending on the applications.

Computer. A computer processes the output of the sensing unit and calculates the motion/gesture tracking results. It can be either an embedded system or a desktop system.

Software. The computer software implements the algorithms and enables the workflows.

An example of configuration for Method One. For one embodiment, as shown in FIG. 4, as an eye tracking and gaze point recording system, an image sensor and a spatial orientation sensor are attached to a harness frame worn by the user and is point to an eye of the user. The image sensor is mounted on rigid platform with the spatial orientation sensor. The orientation of the image sensor relative to the spatial orientation sensor does not change.

An example of configuration for Method Two, as shown in FIG. 5, the image sensor is mounted on rigid platform near the eye. The position and orientation of the image sensor relative to the world coordinate system CS-W do not change.

Methods

Method One

Assuming the image sensor and the spatial orientation sensor are mounted on a rigid frame. Their relative orientation does not change.

Assuming $q\_c\_g$ is the quaternion representing the orientation of image sensor coordinate system CS-C in spatial orientation sensor coordinate system CS-S.

Assuming $q\_c\_g$ is known.

At the first head pose, the user look at a gaze point at a distance, $q\_e\_c\_1$ is obtained as the quaternion representing the orientation of eye coordinate system CS-E to image sensor coordinate system CS-C and $q\_g\_w\_1$ is obtained as the orientation of the spatial orientation sensor coordinate system CS-Q in the world coordinate system CS-W in the first head pose.

After the user re-orients the head to a second pose but still looks at the same gaze point, $q\_e\_c\_2$ is obtained as the quaternion representing the orientation of eye coordinate system CS-E to image sensor coordinate system CS-C and $q\_g\_w\_2$ is obtained as the orientation of the spatial orientation sensor coordinate system CS-G in the world coordinate system CS-W in the second head pose.

The orientation $q\_e\_w\_1$ of the eye coordinate system CS-E in world coordinate system in the first head pose can be obtained as:

$$q\_e\_g\_1 = q\_\text{prd2}(q\_c\_g, q\_e\_c\_1)$$

$$q\_e\_w\_1 = q\_\text{prd2}(q\_g\_w\_1, q\_e\_g\_1)$$

The orientation $q\_e\_w\_2$ of the eye coordinate system CS-E in world coordinate system
in the second head pose can be obtained as:

$$q\_e\_g\_2 = q\_\text{prd2}(q\_c\_g, q\_e\_c\_2)$$

$$q\_e\_w\_2 = q\_\text{prd2}(q\_g\_w\_2, q\_e\_g\_2)$$

The visual axis can be represented as a unit 3D vector $v\_a\_e$ in eye coordinate system CS-E. It is assumed $v\_a\_e$ does not change for a given eye.

Assuming $v\_a\_w\_1$ is the visual axis unit vector in world coordinate system CS-W in first head pose. Assuming $v\_a\_w\_2$ is visual axis unit vector in world coordinate system CS-W in second head pose.

$$v\_a\_w\_1 = \text{qvq\_trans}(q\_e\_w\_1, v\_a\_e)$$

and:

$$v\_a\_w\_2 = \text{qvq\_trans}(q\_e\_w\_2, v\_a\_e)$$

Because at both the first and second head poses, the user is looking at the same gaze point, therefore:

$$v\_a\_w\_1=v\_a\_w\_2$$

and:

$$\text{qvq\_trans}(q\_e\_w\_1,v\_a\_e)=\text{qvq\_trans}(q\_e\_w\_2,v\_a\_e)$$

It can be also represented as:

$$\text{mv\_prd}(m\_e\_w\_1,v\_a\_e)=\text{mv\_prd}(m\_e\_w\_2,v\_a\_e)$$

$$m\_e\_w\_1=m\_\text{frm}\_q(q\_e\_w\_1)$$

$$m\_e\_w\_2=m\_\text{frm}\_q(q\_e\_w\_2)$$

therefore:

$$v\_a\_e=\text{mv\_prd}(m\_ei\_w\_\text{one},v\_a\_e)$$

where: m_ei_w_one=m_prd (m_rev (m_e_w_1), m_e_w_2) and m_e_w_1, m_e_w_2 and m_ei_w_one are 3×3 rotation matrix The visual axis unit vector v_a_e in eye coordinate system CS-E can be obtained as $$v\_a\_e=m\_ei(m\_ei\_w\_\text{one}).$$

Method Two

Assuming the image sensor is mounted on a rigid frame. The orientation of the image sensor coordinate system CS-C in world coordinate system CS-W does not change.

At the first head pose, the user look at a gaze point at a distance, q_e_c_1 is obtained as the quaternion representing the orientation of eye coordinate system CS-E to image sensor coordinate system CS-C. Assuming q_e_c_1 can be obtained.

With the eye keep looking at the same gaze point, the user re-orient the head to a second pose. q_e_c_2 is obtained as the quaternion representing the orientation of eye coordinate system CS-E to image sensor coordinate system CS-C. Assuming q_e_c_2 can be obtained.

The orientation q_e_w_1 of the eye coordinate system CS-E in world coordinate system in the first head pose can be obtained as:

$$q\_e\_w\_1=q\_\text{prd2}(q\_c\_w,q\_e\_c\_1)$$

The orientation q_e_w_2 of the eye coordinate system CS-E in world coordinate system in the second head pose can be obtained as:

$$q\_e\_w\_2=q\_\text{prd2}(q\_c\_w,q\_e\_c\_2)$$

where q_c_w is the orientation of the image sensor coordinate system CS-C in the world coordinate system. It can be canceled out in the following steps.

The visual axis can be represented as a unit 3D vector v_a_e in eye coordinate system CS-E. It is assumed v_a_e does not change for a given person.

Assuming v_a_w_1 is the visual axis unit vector in world coordinate system CS-W in first head pose. Assuming v_a_w_2 is visual axis unit vector in world coordinate system CS-W in second head pose.

$$v\_a\_w\_1=\text{qvq\_trans}(q\_e\_w\_1,v\_a\_e)$$

and:

$$v\_a\_w\_2=\text{qvq\_trans}(q\_e\_w\_2,v\_a\_e)$$

Because at both the first and second head poses, the user is looking at the same gaze point, therefore:

$$v\_a\_w\_1=v\_a\_w\_2$$

and:

$$\text{qvq\_trans}(q\_e\_w\_1,v\_a\_e)=\text{qvq\_trans}(q\_e\_w\_2,v\_a\_e)$$

It can be also represented as:

$$\text{mv\_prd}(m\_e\_w\_1,v\_a\_e)=\text{mv\_prd}(m\_e\_w\_2,v\_a\_e)$$

$$m\_e\_w\_1=m\_\text{frm}\_q(q\_e\_w\_1)$$

$$m\_e\_w\_2=m\_\text{frm}\_q(q\_e\_w\_2)$$

and from:

$$m\_e\_w\_1=m\_\text{prd}(m\_c\_w,q\_e\_c\_1)$$

$$m\_e\_w\_2=m\_\text{prd}(m\_c\_w,q\_e\_c\_2)$$

$$m\_c\_w=m\_\text{frm}\_q(q\_c\_w)$$

m_c_w can be cancelled out, we can get:

$$\text{mv\_prd}(m\_e\_c\_1,v\_a\_e)=\text{mv\_prd}(m\_e\_c\_2,v\_a\_e)$$

$$m\_e\_c\_1=m\_\text{frm}\_q(q\_e\_c\_1)$$

$$m\_e\_c\_2=m\_\text{frm}\_q(q\_e\_c\_2)$$

$$m\_c\_w=m\_\text{frm}\_q(q\_c\_w)$$

therefore:

$$v\_a\_e=\text{mv\_prd}(m\_ei\_w\_\text{two},v\_a\_e)$$

where: m_ei_w_two=m_prd (m_rev(m_e_c_1), m_e_c_2) and m_e_w_1, m_e_w_2 and m_ei_w_two are 3×3 rotation matrix The visual axis unit vector v_a_e in eye coordinate system CS-E can be obtained as $$v\_a\_e=m\_ei(m\_ei\_w\_\text{two})$$

APPENDIX

The mathematical tools listed in Appendix are used in the Methods section.

A1. Coordinate Systems

Figure 1:
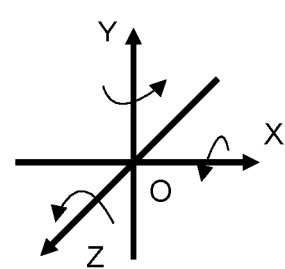
FIG. 1 shows a 3D coordinate system.

A1.1. A 3D coordinate system has three axes, X, Y and Z, as shown in FIG. 1. Right hand rule is applied for the order of the axes and the positive rotation directions.

A1.2. Having the image sensor sensing direction facing forward, the image sensor coordinate system has x axis pointing to the right, y axis pointing to the top and z axis pointing to the opposite direction of the lens. For a single camera image sensor setup, its origin is at the optic center of the camera.

A1.3. Having the eye facing forward, the eye coordinate system CS-E has x axis pointing to the right, y axis pointing to the top, z axis aligned with optical axis and pointing to the back side of the eyeball. Its origin is at the center of the eyeball.

A1.4. Having the head facing forward, the head coordinate system has x axis pointing to the right, y axis pointing to the top and z axis pointing to the opposite direction of the nose.

A1.5. A point in 3D Coordinates can be represented by a 3D vector v=(x, y, z). The vector is from the origin of the coordinate system to the position of the point.

A1.6. Position of a 3D object in a 3D coordinate system is describe as (x, y, z). Orientation a 3D object in a 3D coordinate system can be describe with quaternion, 3×3 matrix, Euler angles etc. The pose of a 3D object in a 3D coordination system is described as its position and its orientation.

A2. Quaternion, 3D Vector, 3×3 Matrix and 2D vector mathematics

A2.1.1. A quaternion has four elements $$q=(w,x,y,z)$$

A2.1.2. An identity quaternion:

$$q=q\_idt(q)=(1,0,0,0)$$

A2.1.3. The conjugation of a quaternion:

$$q\_cnj(q)=(w,-x,-y,-z)$$

A2.1.4. The length of a quaternion:

$$q\_len(q)=sqrt(w*w+x*x+y*y+z*z)$$

sqrt( ) is square root of a floating point number.

A2.1.5. A unit quaternion has a length of 1
To unitize a quaternion q:

$$u=q\_uni(q)$$

where $$q=(w,x,y,z)$$

$$u=(uw,ux,uy,uz)$$

$$uw=x/len$$

$$ux=x/len$$

$$uy=y/len$$

$$uz=z/len$$

$$len=q\_len(q)$$

A2.1.6. The product of two quaternions q and p $$t=q\_prd2(q,p)=q*p$$

where $$q=(qw,qx,qy,qz)$$

$$p=(pw,px,py,pz)$$

$$t=(tw,tx,ty,tz)$$

and $$tw=(qw*pw-qx*px-qy*py-qz*pz)$$

$$tx=(qw*px+qx*pw+qy*pz-qz*py)$$

$$ty=(qw*py-qx*pz+qy*pw+qz*px)$$

$$tz=(qw*pz+qx*py-qy*px+qz*pw)$$

As a quaternion can be used to represent a rotation transformation, if q2 is product of two quaternion q2=q_prd2(q1, q0), then applying q2 as an orientation transformation is equivalent to applying q0 and then q1.

A2.1.7 The product of three quaternions $$q=q\_prd3(q1,q2,q3)=q\_prd2(q1,q\_prd2(q2,q3))$$

A2.2.1 A 3D vector has three elements $$v=(x,y,z)$$

A2.2.2 The length of a 3D vector:

$$v\_len(v)=sqrt(x*x+y*y+z*z)$$

A2.2.3 A unit 3D vector has a length of 1
To unitize a 3D vectors v:

$$u=v\_uni(v)$$

where $$v=(x,y,z)$$

$$u=(ux,uy,uz)$$

$$ux=x/len$$

$$uy=y/len$$

$$uz=z/len$$

$$len=v\_len(v)$$

A2.3.1. 3×3 matrix $$m = \begin{pmatrix} Xx & Yx & Zx \\ Xy & Yy & Zy \\ Xz & Yz & Zz \end{pmatrix}$$

A2.3.2. identity 3×3 matrix $$m = m\_idt() == \begin{pmatrix} 1 & 0 & 0 \\ 0 & 1 & 0 \\ 0 & 0 & 1 \end{pmatrix}$$

A2.3.3. matrix subtraction $$m2 = m\_sub(m1, m0) = m1 - m0 = \begin{pmatrix} Xx1 - Xx0 & Yx1 - Yx0 & Zx1 - Zx0 \\ Xy1 - Xy0 & Yy1 - Yy0 & Zy1 - Zy0 \\ Xz1 - Xz0 & Yz1 - Yz0 & Zz1 - Zz0 \end{pmatrix}$$

$$m1 = \begin{pmatrix} Xx1 & Xy1 & Xz1 \\ Xy1 & Yy1 & Zy1 \\ Zx1 & Zy1 & Zz1 \end{pmatrix}$$

$$m0 = \begin{pmatrix} Xx0 & Xy0 & Xz0 \\ Xy0 & Yy0 & Zy0 \\ Zx0 & Zy0 & Zz0 \end{pmatrix}$$

A2.3.4. matrix vector multiplication $$vd = mv\_prd(m, v) = m * vs$$

$$m = \begin{pmatrix} Xx & Yx & Zx \\ Xy & Yy & Zy \\ Xz & Yz & Zz \end{pmatrix}$$

$$vs = (x, y, z)$$

$$vd = (dx, dy, dz)$$

where:

$$dx = Xx * x + Yx * x + Zx * z$$

$$dy = Xy * x + Yy * y + Zy * z$$

$$dz = Xz * x + Yz * y + Zz * z$$

11

A2.3.5. matrix from quaternion $m=m\_frm\_q(q)$ $q=(qw,qx,qy,qz)$ where m is a 3×3 matrix $$m = \begin{pmatrix} Xx & Yx & Zx \\ Xy & Yy & Zy \\ Xz & Yz & Zz \end{pmatrix}$$

and $Xx = 1.0f - 2.0f*qy*qy - 2.0f*qz*qz$ $Xy = 2.0f*qx*qy + 2.0f*qw*qz$ $Xz = 2.0f*qx*qz*-2.0f*qw*qy$ $Yx = 2.0f*qx*qy - 2.0f*qw*qz$ $Yy = 1.0f - 2.0f*qx*qx - 2.0f*qz*qz$ $Yz = 2.0f*qy*qz + 2.0f*qw*qx$ $Zx = 2.0f*qx*qz + 2.0f*qw*qy$ $Zy = 2.0f*qy*qz - 2.0f*qw*qx$ $Zz = 1.0f - 2.0f*qx*qx*2.0f - qy*qy$

A2.3.6. Transform a 3D vectors v with a quaternion q:

$vd=qvq\_trans(q,vs)=mv\_prd(m,vs)$ where
q is a quaternion
vs is the source 3D vector
vd is the result 3D vector
m is a 3×3 matrix $m=m\_frm\_q(q)$

A2.3.7. Matrix Transpose $mt=m\_inv(m)$ where m, mt are 3×3 matrix $$m = \begin{pmatrix} Xx & Yx & Zx \\ Xy & Yy & Zy \\ Xz & Yz & Zz \end{pmatrix}$$

$$mt = \begin{pmatrix} Xxt & Yxt & Zxt \\ Xyt & Yyt & Zyt \\ Xzt & Yzt & Zzt \end{pmatrix}$$

and $Xxt = Xx;$ $Yxt = Xy;$ $Zxt = Xz;$ $Xyt = Yx;$ $Yyt = Yy;$ $Zyt = Yz;$ $Xzt = Zx;$ $Yzt = Zy;$ $Zzt = Zz;$

A2.3.7. Matrix Inverse $mi=m\_inv(m)$

12 where m, mi are 3×3 matrix $$m = \begin{pmatrix} Xx & Yx & Zx \\ Xy & Yy & Zy \\ Xz & Yz & Zz \end{pmatrix}$$

$$mi = \begin{pmatrix} Xxi & Yxi & Zxi \\ Xyi & Yyi & Zyi \\ Xzi & Yzi & Zzi \end{pmatrix}$$

and $AXx = Yy*Zz - Zy*Yz;$ $AYx = Xy*Zz - Zy*Xz;$ $AZx = Xy*Yz - Yy*Xz;$ float $det = Xx*AXx - Yx*AYx + Zx*AZx;$ $AXy = Yx*Zz - Zx*Yz;$ $AYy = Xx*Zza - Zx*Xz;$ $AZy = Xx*Yz - Yx*Xz;$ $AXz = Yx*Zy - Zx*Yy;$ $AYz = Xx*Zy - Zx*Xy;$ $AZz = Xx*Yy - Yx*Xy;$ $AYx = -AYx;$ $AXy = -AXy;$ $AZy = -AZy;$ $AYz = -AYz;$ $Xxi = AXx/det;$ $Yxi = AXy/det;$ $Zxi = AXz/det;$ $Xyi = AYx/det;$ $Yyi = AYy/det;$ $Zyi = AYz/det;$ $Xzi = AZx/det;$ $Yzi = AZy/det;$ $Zzi = AZz/det;$

A2.3.8. Eigen vector of a matrix $v\_ei=m\_ei(m,r)$ where m is a 3×3 matrix $$m = \begin{pmatrix} Xx & Yx & Zx \\ Xy & Yy & Zy \\ Xz & Yz & Zz \end{pmatrix}$$

v is the is a 3D vector $v=(x,y,z)$ r is a number
and:

$$v=v\_uni(vk)$$

where:

$$vk=(xk,yk,zk)$$

and one way to solve it is:

$$xk=1.0$$

$$yk=(c*d-a*f)/(b*f-c*e)$$

$$zk=(a*e-b*d)/(b*f-c*e)$$

where:

$$a=Xx-r;$$

$$b=Yx;$$

$$c=Zx;$$

$$d=Xy;$$

$$e=Yy-r;$$

$$f=Zy;$$

$$g=Xz;$$

$$h=Yz;$$

$$l=Zz-r.$$

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A computer program product comprising a non-transitory computer readable medium having instructions recorded thereon, the instructions when executed by a computer implementing a method comprising:

while a person's head is at a first pose and the person's eye is gazing at a point in a 3D space, obtaining a first orientation of the eye with respect to an image sensor and a first orientation of a spatial orientation sensor with respect to the 3D space;

while the person's head is at a second pose and the person's eye is gazing at the point, obtaining a second orientation of the eye with respect to the image sensor and a second orientation of the spatial orientation sensor with respect to the 3D space;

wherein the first pose and the second pose are different;

determining an angular offset between a visual axis of the eye and an optical axis of the eye, or an angular offset between a line of sight of the eye and the optical axis of the eye, based on:

the first orientation of the eye, the first orientation of the spatial orientation sensor, the second orientation of the eye, the second orientation of the spatial orientation sensor, and an orientation of the image sensor relative to the spatial orientation sensor or an orientation of the spatial orientation sensor relative to the image sensor;

wherein the image sensor and the spatial orientation sensor do not move relative to each other.

2. The computer program product of claim 1, wherein the image sensor is configured to image the eye.

3. The computer program product of claim 1, further comprising capturing a first image of the eye while the head is at the first pose and the eye is gazing at the point in the 3D space, wherein obtaining the first orientation of the eye with respect to the image sensor is based on the first image.

4. The computer program product of claim 1, wherein the image sensor does not move relative to the head.

5. The computer program product of claim 1, wherein determining the angular offset between the visual axis of the eye and the optical axis of the eye or the angular offset between the line of sight of the eye and the optical axis of the eye is further based on a difference of positions of the eye relative to the image sensor while the person's head is at the first pose and at the second pose.

6. The computer program product of claim 1, wherein determining the angular offset between the visual axis of the eye and the optical axis of the eye or the angular offset between the line of sight of the eye and the optical axis of the eye is further based on positions of the eye relative to the 3D space while the person's head is at the first pose and at the second pose.

7. The computer program product of claim 1, wherein determining the angular offset between the visual axis of the eye and the optical axis of the eye or the angular offset between the line of sight of the eye and the optical axis of the eye is further based on positions of the image sensor relative to the 3D space while the person's head is at the first pose and at the second pose.

8. A computer program product comprising a non-transitory computer readable medium having instructions recorded thereon, the instructions when executed by a computer implementing the method a method comprising:

while a person's head is at a first pose and the person's eye is gazing at a point in a 3D space, obtaining a first orientation of the eye with respect to an image sensor;

while the person's head is at a second pose and the person's eye is gazing at the point, obtaining a second orientation of the eye with respect to the image sensor;

wherein the first pose and the second pose are different;

determining an angular offset between a visual axis of the eye and an optical axis of the eye, or an angular offset between a line of sight of the eye and the optical axis of the eye, based on the first orientation of the eye and the second orientation of the eye;

wherein the image sensor does not move relative to the 3D space.

9. The computer program product of claim 8, wherein the image sensor is configured to image the eye.

10. The computer program product of claim 8, further comprising capturing a first image of the eye while the head is at the first pose and the eye is gazing at the point in the 3D space, wherein obtaining the first orientation of the eye with respect to the image sensor is based on the first image.

11. The computer program product of claim 8, wherein determining the angular offset between the visual axis of the eye and the optical axis of the eye or the angular offset between the line of sight of the eye and the optical axis of the eye is further based on a difference of positions of the eye relative to the image sensor while the person's head is at the first pose and at the second pose.

12. The computer program product of claim 8, wherein determining the angular offset between the visual axis of the eye and the optical axis of the eye or the angular offset between the line of sight of the eye and the optical axis of the eye is further based on positions of the eye relative to the 3D space while the person's head is at the first pose and at the second pose.

13. The computer program product of claim 8, wherein determining the angular offset between the visual axis of the eye and the optical axis of the eye or the angular offset between the line of sight of the eye and the optical axis of the eye is further based on positions of the image sensor relative to the 3D space while the person's head is at the first pose and at the second pose.

* * * * *